United States Patent [19]

Sagredos et al.

[11] Patent Number: 4,588,831
[45] Date of Patent: May 13, 1986

[54] PLATINUM COMPLEX COMPOUNDS OF SUBSTITUTED 5,8-DIHYDROXYL-1,4-NAPHTHOQUINONE, AND PROCESS FOR THEIR PRODUCTION AND USE

[75] Inventors: Angelos N. Sagredos, Hamburg, Fed. Rep. of Germany; Vassilios P. Papageorgiou, Panorama/Thessaloniki; Antonius S. Mellidis, Salonica, both of Greece

[73] Assignee: NATEC, Fed. Rep. of Germany

[21] Appl. No.: 669,965

[22] Filed: Nov. 9, 1984

[51] Int. Cl.[4] ............................................. C07F 15/00
[52] U.S. Cl. ............................ 556/137; 260/366; 549/417
[58] Field of Search ................... 260/429 R; 556/137

[56] References Cited

U.S. PATENT DOCUMENTS

| | | | |
|---|---|---|---|
| 3,892,790 | 7/1975 | Tobe et al. | 260/429 R |
| 3,904,663 | 9/1975 | Tobe et al. | 260/429 R |
| 4,140,707 | 2/1979 | Cleare et al. | 260/429 R |
| 4,200,583 | 4/1980 | Kidani et al. | 260/429 R X |
| 4,283,342 | 8/1981 | Yolles | 260/429 R X |

FOREIGN PATENT DOCUMENTS 1574397  9/1980  United Kingdom .

OTHER PUBLICATIONS

Chemical Abstracts 94 157066q (1981).
Chemical Abstracts 94 157067r (1981).
Rosenberg, Naturwissenschaften 1973, 399-406.
Yolles et al., ACS-Symposium 1982, 233-241.
Chem. Abstracts, 1982, 97:48587b.
Chem. Abstracts, 1981, 95:61832f.
Chem. Abstracts, 1980, 93:7882t.
Chem. Abstracts, 1978, 88:15897p and 88:44863e.

*Primary Examiner*—Helen M. S. Sneed
*Attorney, Agent, or Firm*—Roylance, Abrams, Berdo & Goodman

[57] ABSTRACT

The invention relates to platinum complexes of the following general formula:

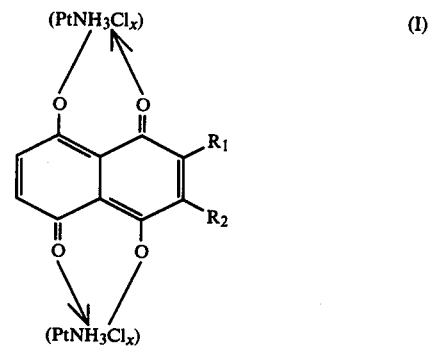

wherein $R_1$ and $R_2$ represent alkyl radicals with 1 to 18 carbon atoms, or $R_1$ or $R_2$ represent a hydrogen atom and $R_2$ or $R_1$ can represent an alkyl radical or a

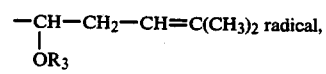

in which $R_3$ is a hydrogen atom or the

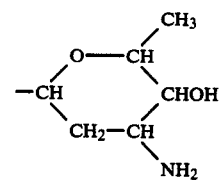

radical or an acyl radical, and $x=1$ or 2.

These compounds can be produced by reaction of an alcohol solution of a 5,8-dihydroxyl-1,4-naphthoquinone of the following formula:

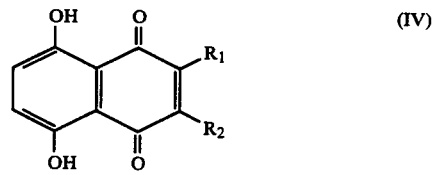

in which the substituents $R_1$ and $R_2$ have the aforementioned meanings, in the presence of a concentrated aqueous ammonia solution, which adjusts the pH over 7, with $K_2PtCl_4$ at room temperature. These platinum complex compounds are characterized by a good antitumor effect with low toxicity.

6 Claims, No Drawings

PLATINUM COMPLEX COMPOUNDS OF SUBSTITUTED 5,8-DIHYDROXYL-1,4-NAPHTHOQUINONE, AND PROCESS FOR THEIR PRODUCTION AND USE

BACKGROUND OF THE INVENTION

The invention relates to platinum complex compounds of substituted 5,8-dihydroxyl-1,4-naphthoquinones and also to a process for their manufacture and their use as materials with an antitumor effect.

It is known that a number of platinum compounds, particularly cis-dichloro-diamino-platinum (II), used in clinics under the name cis-DDP, along with its generally toxic effect and also bactericidal, virusidal and immuno-suppressive effects, also has an antitumor effect (Rosenberg, Naturwissenschaften 1973, 399–406). It is also known that complexes of this quadratic planar platinum compound with anthraquinone derivatives such as quinizarin and doxorubizin discharge the cis-DDP in the animal body slowly, and its toxicity is greatly decreased. While more than 7 mg of the free cis-DDP/kg of mouse has a toxic effect, doses of 20 mg of cis-DDP/kg mouse can be applied by using the new complex compounds, and this promotes both an increase of the average survival time and also an increased number of cases of healing. In the course of the testing of the pharmacological effect of the cited platinum-anthraquinone complexes, for the purpose of clarification of the chemical bonding ratios, some relatively simple alpha-hydroxylquinones were also complexed with platinum, but were tested neither in vitro nor in vivo on tumors or for other pharmacological effect (Yolles et al., ACS-Symposium 1982, 233–241). With these naphthoquinone complexes manufactured only for the structural definition, the complexes involved were:

(I) 5-hydroxyl-1,4-naphthoquinone/cis-DDP complex
(II) 5,8-dihydroxyl-1,4-naphthoquinone/cis-DDP complex.

SUMMARY OF THE INVENTION

It has now been discovered that two other groups of complex compounds of platinum, with 5,8-dihydroxyl-1,4-naphthoquinone derivatives and not known until now, show a still stronger antitumor effect with lower toxicity than the known platinum complex compounds.

The present invention relates to platinum complex compounds of the following general formula:

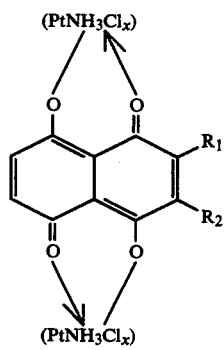

wherein $R_1$ and $R_2$ can be identical or different, and can represent an alkyl radical with 1 to 18 carbon atoms, preferably with 1 to 6 carbon atoms, or either $R_1$ or $R_2$ can represent a hydrogen atom and $R_2$ or $R_1$ can represent an alkyl radical with 1 to 18 carbon atoms, preferably with 1 to 6 carbon atoms, or a

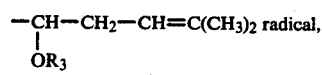

wherein $R_3$ is a hydrogen atom or the radical:

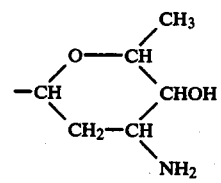

or an acyl radical, preferably derived from angelic acid, e.g.,

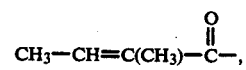

In the platinum complex compounds according to the invention, complex compounds of the following formula are provided

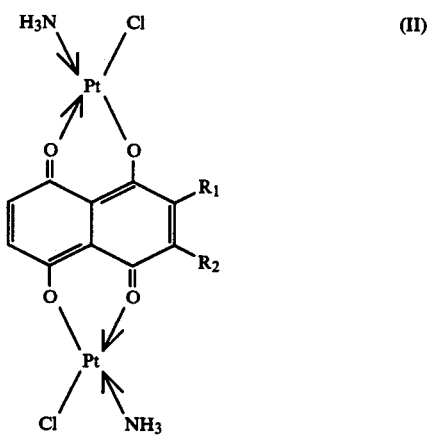

wherein $R_1$ and $R_2$ have the aforementioned meanings, and $x=1$. The invention also relates to complex compounds with double the chlorine content of formula II, i.e. $x=2$, but otherwise with identical structure as formula II. These complex compounds can therefore be defined by the following tautomeric formula:

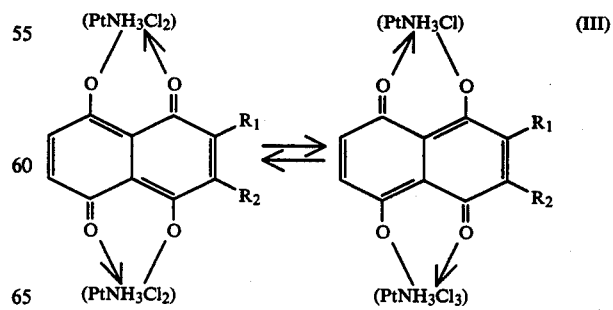

By analytical tests, it has been determined that the organic part of the complex compounds of formula III is identical with the organic part of the corresponding compounds of formula II. The corresponding substituted dihydroxylnaphthoquinones from the complex compounds of formulas II and III, which are identical with the organic original compound which is used, can be removed without difficulty by hydrolysis.

Each type of complex compound (II) or (III) could be produced separately in pure state and be obtained, e.g., if the conditions cited in the following exemplary embodiments could be maintained exactly. They generally accumulate, however, side by side, if the following measures are not maintained.

In the process according to the invention, the corresponding naphthoquinone derivatives of Formula IV, wherein the substituents $R_1$ and $R_2$ (including $R_3$) have aforementioned meanings, are used for the production both of compounds as in Formula II and also for those of Formula III.

The process for the production of the platinum complex compounds of formula I according to the invention is carried out in a manner wherein an alcoholic solution of a 5,8-dihydroxyl-1,4-naphthoquinone of the formula IV

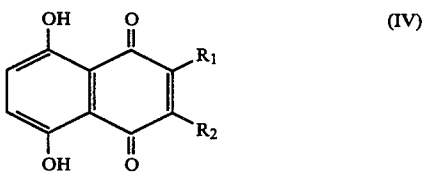

wherein $R_1$ and $R_2$ (including $R_3$) have the aforementioned meanings, the pH value of said solution is set over 7 by addition of concentrated aqueous ammonia solution, and then said solution is reacted with an aqueous solution of $K_2PtCl_4$ at room temperature, and the reaction mixture is stirred continuously for several hours. All stages of the process are preferably carried out at room temperature. Complex formation thus occurs with rearrangement of the double bonds in the double cyclic system, wherein complex compounds of formula I are generally formed with $x=1$ and $x=2$ side by side. By maintenance of certain, relatively narrow pH ranges during the reaction, however, it is possible to govern the reaction to favor the formation of platinum complex compounds of formula I with either $x=1$ or $x=2$. When a substituted 5,8-dihydroxyl-1,4-naphthoquinone (IV) is reacted with an aqueous $K_2PtCl_4$ solution preferably at a pH of 8 to 8.5, essentially platinum complex compounds of formula II ($x=1$) are obtained; if the reaction occurs at a pH of over 10, essentially platinum complex compounds of formula III ($x=2$) are formed.

The formed platinum complex compounds are precipitated as dark powders which can be separated and cleaned in a known manner, for example, by filtration and washing in sequence with water, acetone and an ether, e.g., tetrahydrofuran. Then the cleaned product is dried.

DESCRIPTION OF THE PREFERRED EMBODIMENTS

The following chart shows the naphthoquinones of formula IV as original substance in the various examples (examples 1 and 7 are comparison examples):

| EXAMPLE NO. | $R_1$ | $R_2$ | $R_3$ |
|---|---|---|---|
| 1, 7 | H | H | |
| 2, 8 | H | $CH_3$ | |
| 3, 9 | $CH_3$ | $CH_3$ | |
| 4, 10 | H | $-\underset{OR_3}{CH}-CH_2-CH=C(CH_3)_2$ | (morpholine-like ring with $CH_3$, $CHOH$, $NH_2$) |
| 5, 11 | H | $-\underset{OR_3}{CH}-CH_2-CH=C(CH_3)_2$ | H |
| 6, 12 | H | $-\underset{OR_3}{CH}-CH_2-CH=C(CH_3)_2$ | $-\overset{O}{\overset{\|}{C}}-\underset{CH_3}{\overset{\|}{C}}=CH-CH_3$ |

EXAMPLES 1 TO 6

Production of Platinum Complex Compounds of Formula II

In all of these examples, 1 mMol of the relevant naphthoquinone was dissolved in 100 ml ethanol and adjusted to pH value of 8 by addition of concentrated aqueous ammonia solution. An aqueous solution of 2 mMol $K_2PtCl_4$ in 100 ml of bi-distilled water was added to this ammoniacal alcoholic solution with constant stirring at room temperature and the mixture was stirred continually overnight while still at room temperature. Following concentration on the vapor rotor, the separated platinum complex compound was filtered through a frit and washed a number of times, first with bi-distilled water, then with acetone, and finally with an ether (tetrahydrofuran) in a Soxhlet apparatus to remove unreacted naphthoquinone derivatives and finally dried in the vacuum dessicator.

EXAMPLES 7 TO 12

Production of Platinum Complex Compounds of Formula III

The process differs from that of examples 1 to 6 only in that the alcohol solution of the naphthoquinone (IV)

was set at a pH of 11 before the addition of the K₂PtCl₄ solution.

All of the platinum complex compounds obtained in examples 1 to 12 were dark powders, which decomposed during testing for determination of the melting point, and which are only slightly soluble to insoluble in organic solvents.

The elementary analysis of the compounds which were obtained is summarized in the following Table I, wherein the values calculated from the comparison formulas can also be compared with the results of analysis.

TABLE I

| Example | | Results of the Elementary Analyses | | | | |
|---|---|---|---|---|---|---|
| | | C | H | $NH_3$ | Cl | Pt |
| 1 | Found | 17.92 | 0.64 | 6.61 | 10.4 | 56.0 |
| | Calculated | 17.58 | 0.58 | 4.97 | 10.38 | 57.11 |
| 2 | Found | 18.71 | 0.80 | 5.06 | 10.61 | 54.10 |
| | Calculated | 18.95 | 0.86 | 4.87 | 10.17 | 55.95 |
| 3 | Found | 16.92 | 1.26 | 4.91 | 10.20 | 55.12 |
| | Calculated | 17.29 | 1.12 | 4.78 | 9.97 | 54.85 |
| 4 | Found | 26.70 | 2.91 | 5.14 | 9.23 | 45.25 |
| | Calculated | 28.39 | 2.70 | 3.82 | 7.98 | 43.92 |
| 5 | Found | 25.22 | 1.94 | 4.60 | 10.13 | 48.16 |
| | Calculated | 24.91 | 1.81 | 4.40 | 9.20 | 50.58 |
| 6 | Found | 28.76 | 2.51 | 3.71 | 9.80 | 43.70 |
| | Calculated | 29.21 | 2.33 | 3.93 | 8.20 | 45.18 |
| 7 | Found | 16.31 | 0.61 | 4.73 | 19.40 | 52.00 |
| | Calculated | 15.96 | 0.53 | 4.51 | 18.63 | 51.85 |
| 8 | Found | 17.51 | 0.86 | 4.60 | 17.71 | 49.80 |
| | Calculated | 17.23 | 0.78 | 4.43 | 18.29 | 50.90 |
| 9 | Found | 18.10 | 1.10 | 4.71 | 18.25 | 50.40 |
| | Calculated | 18.46 | 1.02 | 4.35 | 17.96 | 50.00 |
| 10 | Found | 25.65 | 2.83 | 4.12 | 13.70 | 41.89 |
| | Calculated | 26.04 | 2.47 | 3.51 | 14.64 | 40.28 |
| 11 | Found | 21.81 | 1.92 | 4.40 | 15.50 | 48.16 |
| | Calculated | 22.59 | 1.64 | 4.00 | 16.48 | 45.86 |
| 12 | Found | 26.20 | 2.29 | 4.10 | 14.10 | 39.80 |
| | Calculated | 27.00 | 2.14 | 3.64 | 15.00 | 41.75 |

TESTS IN VIVO

The standard test with the Ehrlich Ascites tumor was used on ICR mice for determination of the anticarcinogenic activity of the platinum complex compounds according to the invention. For the experiments, one animal group (10 mice) was used per dose of the platinum-naphthoquinone derivative complex, and two animal groups (20 mice) were used for the comparison tests (a) with cis-DDP (positive control) and (b) without an antitumor material (negative control). The tumor cells as well as the platinum complex compounds were injected intraperitoneally on day zero and respectively on the first and sixth day. The results were summarized in the following Table II.

TABLE II

| Antitumor effect of platinum complex compounds | | |
|---|---|---|
| | Dose in mg Pt complex per kg | Number of "cures" per animal group |
| Negative control | 0 | 0 |
| Positive control | 6 | 4 |
| Platinum complex from Example: | | |
| 1 (comparison) | 20 | 7 |
| 2 | 20 | 8 |
| 3 | 20 | 7 |
| 4 | 30 | 8 |
| 5 | 30 | 8 |
| 6 | 30 | 9 |
| 7 (comparison) | 20 | 5 |
| 8 | 20 | 7 |
| 9 | 15 | 6 |

TABLE II-continued

| Antitumor effect of platinum complex compounds | | |
|---|---|---|
| | Dose in mg Pt complex per kg | Number of "cures" per animal group |
| 10 | 24 | 6 |
| 11 | 24 | 7 |
| 12 | 24 | 8 |

The term "cure" was taken from the National Cancer Institute, U.S.A., and means the number of animals surviving longer than 60 days. The results show that the platinum complex compounds according to the invention as compared with the known antitumor agents of comparison examples 1 and 7 show at least as good, and mostly even better antitumor effect.

What is claimed is:

1. Platinum complex compounds of the general formula:

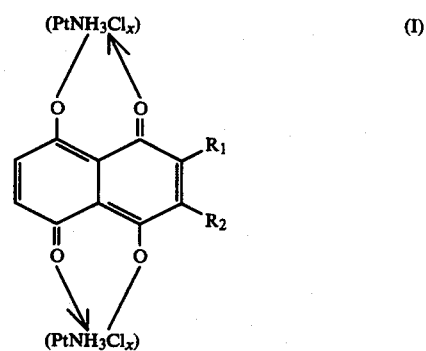

(I)

wherein $R_1$ and $R_2$ can be identical or different, and represent an alkyl radical with 1 to 18 carbon atoms, or either $R_1$ or $R_2$ represent a hydrogen atom or $R_2$ or $R_1$ represents an alkyl radical with 1 to 18 carbon atoms, and

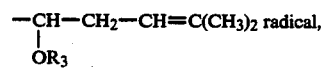

wherein $R_3$ is a hydrogen atom or the:

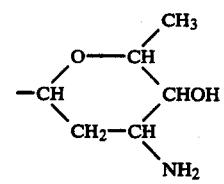

radical or an acyl radical, and $x = 1$ or 2.

2. Platinum complex compounds as defined in claim 1, wherein $R_1$ and $R_2$ are alkyl radicals with 1 to 6 carbon atoms.

3. Platinum complex compounds as defined in claim 1 wherein the acyl radical $R_3$ is an angelic acid radical.

4. Process for the production of platinum complex compounds as defined in claim 1 wherein an alcoholic solution of a 5,8-dihydroxyl-1,4-naphthoquinone of the following formula is provided:

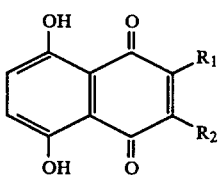

(IV)

wherein the substituents $R_1$ and $R_2$ (including $R_3$) have the aforementioned meanings, a pH value of over 7 is set by addition of concentrated aqueous ammonia solution and then is reacted with an aqueous solution of $K_2PtCl_4$ at room temperature, and the reaction mixture is stirred for several hours continuously, and then the separated platinum complex compounds of the general formula I are filtered out and washed in sequence with water, acetone and, if desired, with an ether and finally are dried.

5. Process as defined in claim 4 wherein the reaction is carried out at a pH of 8 to 8.5 and essentially platinum complex compounds of the formula I with $x=1$ are obtained.

6. Process as defined in claim 4, wherein the reaction occurs at a pH of over 10, and then essentially platinum complex compounds of the formula I with $x=2$ are obtained.

* * * * *